United States Patent [19]

Birtwistle

[11] Patent Number: 5,186,928
[45] Date of Patent: Feb. 16, 1993

[54] SHAMPOO COMPOSITION

[75] Inventor: David H. Birtwistle, Wirral, United Kingdom

[73] Assignee: Chesebrough-Pond's USA Co., Division of Conopco, Inc., Greenwich, Conn.

[21] Appl. No.: 818,496

[22] Filed: Jan. 8, 1992

Related U.S. Application Data

[63] Continuation of Ser. No. 479,325, Feb. 13, 1990, abandoned.

[30] Foreign Application Priority Data

Feb. 20, 1989 [GB] United Kingdom ............... 8903777

[51] Int. Cl.$^5$ ............................................. A61K 7/075
[52] U.S. Cl. ........................................ 424/70; 424/59
[58] Field of Search ............................. 424/59, 70; 252/DIG. 13; 514/777, 847; 536/114

[56] References Cited

U.S. PATENT DOCUMENTS

| | | | |
|---|---|---|---|
| 3,580,853 | 5/1971 | Parran | 252/152 |
| 3,932,610 | 1/1976 | Rudy et al. | 424/70 |
| 4,061,602 | 12/1977 | Oberster et al. | 424/70 X |
| 4,292,212 | 9/1981 | Melby | 424/70 X |
| 4,298,494 | 11/1981 | Parslow et al. | 252/DIG. 13 |
| 4,381,259 | 4/1983 | Homma et al. | 252/DIG. 13 |
| 4,488,564 | 12/1984 | Grollier et al. | 132/7 |
| 4,567,038 | 1/1986 | Ciauclelli et al. | 424/72 X |

FOREIGN PATENT DOCUMENTS

| | | |
|---|---|---|
| 0018717 | 11/1980 | European Pat. Off. . |
| 0093601 | 11/1983 | European Pat. Off. . |
| 0117135 | 8/1984 | European Pat. Off. . |
| 0246854 | 11/1987 | European Pat. Off. . |
| 2627085 | 8/1989 | France . |
| 2129455 | 5/1984 | United Kingdom . |

OTHER PUBLICATIONS

Norda Briefs, No. 464, Feb., 1975.
Chemical Abstracts, vol. 110, No. 16, Apr. 17, 1989, abstract No. 141286z, Columbus, Ohio, US; & JP-A-63 146 999 (Lion Corp.) Jun. 18, 1988.

*Primary Examiner*—Thurman K. Page
*Assistant Examiner*—D. Colucci
*Attorney, Agent, or Firm*—Milton L. Honig

[57] ABSTRACT

A shampoo composition comprises an anionic surfactant, a water-insoluble sunscreen, or mixtures thereof, and a cationic derivative of a polygalactomannan gum. When the sunscreen is normally solid at room temperature, then the composition further comprises a non-volatile solvent for the sunscreen.

11 Claims, 3 Drawing Sheets

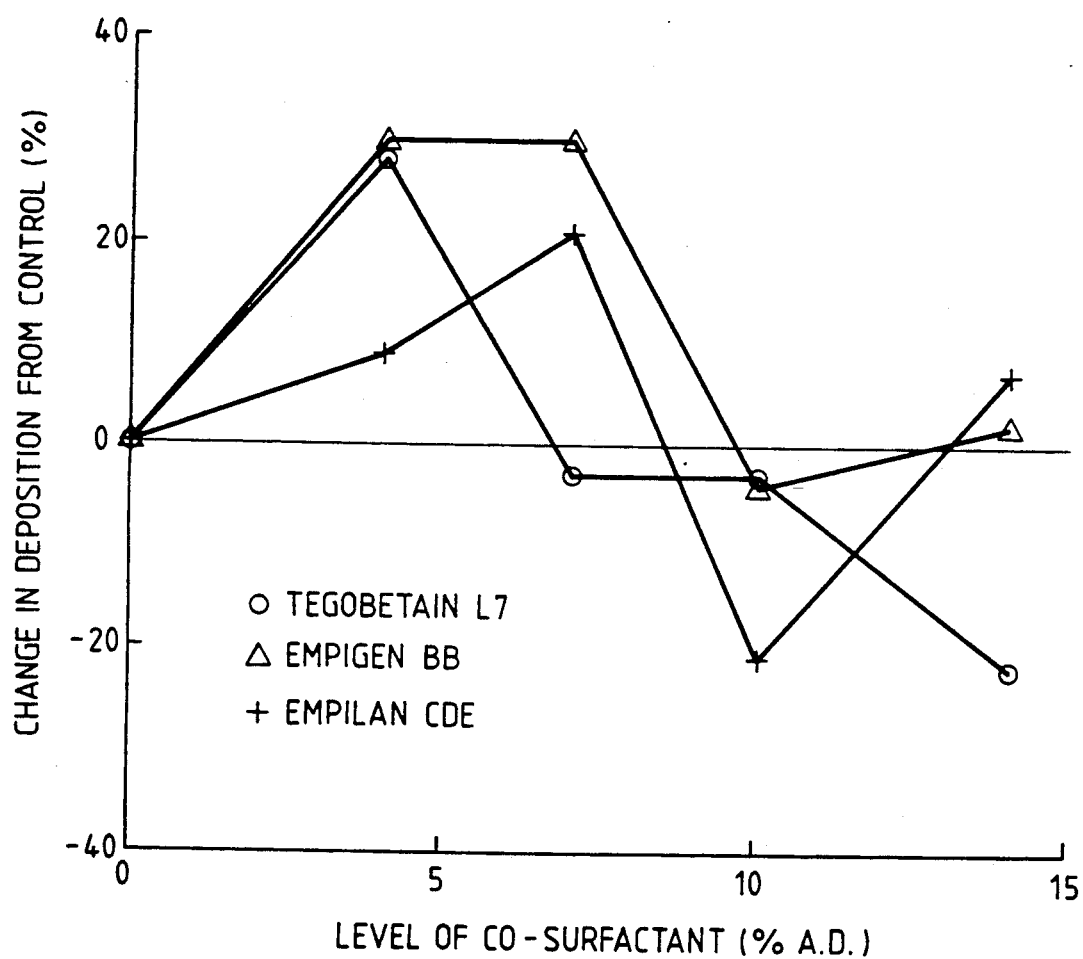

SHAMPOO COMPOSITION

This is a continuation application of Ser. No. 07/479,325 filed Feb. 13, 1990, now abandoned.

BACKGROUND OF INVENTION

The present invention relates to shampoo compositions, and more particularly to shampoo compositions containing sunscreen materials to protect the hair from the harmful effects of sunlight.

Dark hair exposed to sunlight fades, oriental black hair takes on a reddish tinge, and blond hair tends to yellow. The hair becomes rougher and drier to the touch after prolonged exposure to sunlight and also tends to lose its glossy appearance.

The hair can be protected from damage by exposure to sunlight by coating the hair fibres with an effective sunscreen.

It is reported, for example, in U.S. Pat. No. 4 488 564 (L'Oreal) that ultra-violet (UV) filters can be added to shampoo compositions to combat the adverse effects of sunlight on the composition itself. Such compositions tend to fade and to destabilise if left exposed to sunlight for long periods of time. The UV filters used are generally water-soluble, and present in very small amounts.

EP 117 135 (Johnson and Johnson) discloses the use of a water-soluble non-particulate sunscreen, especially para-amino benzoic acid, in a shampoo composition which contains an anionic nitrogen-containing polymer.

We have found however, that sunscreens which are water-soluble do not confer a significant degree of protection on the hair when used in shampoo compositions. These sunscreens are easily removed from the hair in the final rinse step of the washing procedure.

Detergent compositions, for example shampoos, comprising an anionic surfactant, water-insoluble particles and a cationic polymer have been described in U.S. Pat. No. 3 580 853 (Parran). In the detergent compositions described in that patent the cationic polymers are water-soluble cationic nitrogen containing polymers having a molecular weight within the range from 2,000 to 3,000,000 and have a cationic charge density greater than 0.001 in aqueous solution. The "cationic charge density" of a polymer as that term is used in the U.S. patent, refers to the ratio of the number of positive charges on a monomeric unit of which the polymer is comprised to the molecular weight of the monomeric unit. The cationic charge density multiplied by the polymer molecular weight determines the number of positively charged active sites of a given polymer chain. The Parran patent states that the cationic polymer can be employed in the detergent composition at a concentration within the range from about 0.1% to about 10% by weight, preferably from about 0.25% to about 4.0% by weight.

We have investigated the mode of action of the enhancement of deposition of particulate materials from liquid detergent compositions of the Examples of the Parran patent containing an anionic surfactant and it appears that the enhancement derives from the presence in the washing composition of a complex between the anionic surfactant and the cationic polymer which is formed upon dilution of the detergent composition. The formation of complexes between cationic polymers and anionic surfactants is well-known and is described in Norda Briefs, No. 464, Feb., 1975. This article mentions that such complexes may be solubilised at increased surfactant levels and also refers to the deposition of the water-insoluble complex onto the hair during the shampooing process. The Norda Briefs article refers in particular to those complexes formed using the quarternary nitrogen-substituted cellulose ether derivatives (available commerically under the trade name Polymer JR) which the Parran patent states as particularly efficacious for enhancing the deposition of particulate substances.

Our experiments have indicated that in the Parran formulations comprising an anionic surfactant, complexes between the cationic polymer and anionic surfactant precipitate or separate upon dilution during use and that it is essential for this to occur if an enhancement in the deposition of the particulate substance is to be obtained from the Parran compositions containing an anionic surfactant. While precipitation of the complex and its deposition onto the hair may give a benefit in its own right, for such deposition leads to improved hair condition, more particularly improved ease of combing, such deposition of substantial amounts of cationic polymer is not always desired by the user.

Washing compositions comprising an anionic surfactant, a water-insoluble particulate substance and a water-soluble cationic polymer are described in EP 93 601 (Unilever, Sime). The compositions described contain non-cellulose cationic polymer having a cationic charge density (as defined above) of from 0.0001 to 0.0017 and a molecular weight of from 2,000 to 3,000,000.

The particulate substance may comprise oily materials which are pre-emulsified in a solution of anionic surfactant and stabilised using emulsifier to give oil "particles" having an average particle diameter of from 0.2 to 50 $\mu$m.

It is believed that the cationic polymer forms a coating on the surface of the water-insoluble particles which coating has loops which extend into the detergent system, providing positively charged bridges for attachment to negative sites on the substrate. It is essential in the Sime patent that formation of a water-insoluble complex between the cationic polymer and anionic surfactant is avoided, and this is achieved by using low concentrations of polymer having a low cationic charge density, and high concentrations of anionic surfactant. Use of higher concentrations of cationic polymer is said to give precipitation of a cationic/anionic complex which is undersirable for deposition of the particles.

We have found that deposition of water-insoluble normally-liquid sunscreens which have not been pre-emulsified can be achieved at concentrations of cationic polymer which also show conditioning benefit. These liquid sunscreens can be added to shampoos to give a clear solution, in which the sunscreen is solubilised in the micelle of the surfactant, and is not present in particulate or droplet form. It was therefore not expected to obtain enhanced deposition using the Parran or Sime technology. However, the Applicant has found a class of polymer (quaternised polygalactomannan gums) which enhances deposition. The precise mechanism is uncertain, but differs from that of Parran or Sime as no particle or phase separation is necessary for the effect to be seen.

BRIEF SUMMARY OF THE INVENTION

It has now been found that enhanced levels of sunscreen can be deposited on hair surfaces using a shampoo which contains a cationic polymer and water insoluble sunscreens.

Accordingly the invention provides an aqueous shampoo composition comprising, in addition to water,
(a) an anionic surfactant,
(b) a water-insoluble sunscreen or mixtures thereof, and
(c) a cationic derivative of a polygalactomannan gum,
with the proviso that when the sunscreen is one which is in the form of a solid at 20° C., the composition further comprises a non-volatile solvent for the solid sunscreen.

DETAILED DESCRIPTION OF THE INVENTION

(a) Anionic Surfactant

The composition according to the invention comprises an anionic surfactant, examples of which are alkyl ether sulphate, alkyl sulphate or mixtures thereof. Commonly used anionic surfactants are $C_{10}$ to $C_{18}$ alkyl sulphates, and $C_{10}$ to $C_{18}$ alkyl ether sulphates containing 1 to 5, preferably 2 or 3 moles of ethylene oxide. These surfactants are generally employed in the form of their sodium, potassium, ammonium or mono-, di-or tri-ethanolamine salts. Examples of these surfactants are sodium lauryl ether sulphate (2EO), sodium lauryl ether sulphate (3EO), potassium lauryl ether sulphate (2EO) and ammonium lauryl ether sulphate (3EO), sodium lauryl sulphate, ammonium lauryl sulphate and mono-, di-and tri-ethanolamine lauryl sulphates.

Further suitable anionic surfactants include dialkyl sulphosuccinates having the structure:

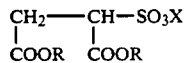

where R represents the same or different straight chain or branched chain alkyl groups having from 4 to 12 carbon atoms; and X is a solubilising cation chosen from alkali metal, ammonium, substituted ammonium and magnesium.

Particularly preferred dialkyl sulphosuccinates include those where R represents $C_6$ and/or $C_8$ alkyl groups.

Still further suitable anionic surfactants include α-olefin sulphonates, alkyl sarcosinates, alkyl monoglyceride sulphates, alkyl monoglyceride sulphonates, alkyl benzene sulphonates, monoalkylether sulphosuccinates, alkyl ether carboxylates, acyl isethionates and acyl methyl taurides.

The amount of anionic surfactant present in the shampoo of the invention will depend on the product form of the shampoo. For example, when the shampoo is a propellant-free liquid or gel intended to be poured, pumped or otherwise dispensed from a bottle or similar container or from a sachet, then the shampoo will generally contain from 2 to 30%, preferably from 10 to 20% by weight of anionic surfactant. When, however, the shampoo is in the form of a liquid or gel containing a gaseous liquefiable propellant, intended to be dispensed from an aerosol can, generally as mousse, then the shampoo concentrate, that is that part of the product without propellant, will generally contain from 2 to 40%, preferably from 10 to 30% by weight of anionic surfactant.

Having regard to the product form of the shampoo, it can be stated generally that shampoos containing less than about 2% by weight of anionic surfactant are likely in use to produce insufficient lather while shampoos containing more than 40% by weight of anionic surfactant may be too thick to apply conveniently to the hair and may also degrease the hair to an undesirably excessive degree.

b) Sunscreen

The composition of the invention also comprises a water-insoluble sunscreen, or a mixture thereof, preferably in an amount of from 0.2 to 5% by weight, most preferably from 0.3 to 2.0% by weight.

If the composition comprises less than 0.2% by weight of the sunscreen, little benefit will be obtained, and if greater than 5% is present, it is unlikely that additional benefit will be obtained.

The water-insoluble sunscreens are either liquid at 20° C. (hereinafter referred to as 'normally liquid sunscreens') or they are solid at 20° C. (hereafter referred to as 'normally solid sunscreens').

Examples of preferred normally-liquid sunscreens are cinnamates, such as 2-ethylhexyl-p-methoxy cinnamate, sold commercially as Parsol MCX, 2-ethoxy ethyl-p-methoxy cinnamate, sold commercially as Giv-Tan F and isoamyl-p-methoxy cinnamate, sold commercially as Neo-Heliopan E1000.

Examples of preferred normally solid sunscreens are benzophenone derivatives such as 4,4'-tetrahydroxybenzophenone, sold commercially as Uvinul D50, and 2-hydroxy-4-methoxy-benzophenone, sold commercially as Eusolex 4360, dibenzoyl methane derivatives such as t-butyl-4-methoxydibenzoyl methane, sold commercially as Parsol 1789, and isopropyldibenzoyl methane, sold commercially as Eusolex 8020.

When the sunscreen in the composition comprises a normally solid sunscreen, there must also be present in the composition a non-volatile solvent to dissolve this sunscreen. This is because a normally-solid sunscreen has a tendency to solidify on the hair in such a manner that coverage of the hair is uneven and maximum benefit of sun protection is not achieved. This solvent may be a normally liquid sunscreen or another non-aqueous non volatile solvent. The normally solid sunscreen and the solvent therefore may be added separately during manufacture of the shampoo or the normally solid sunscreen may be pre-dissolved in the solvent.

Examples of non-volatile solvents for use with normally solid sunscreens in the compositions of the invention are organic esters such as, isopropyl myristate and benzyl benzoate. It is however preferred that the solvent for the normally solid sunscreen is a normally liquid sunscreen.

(c) The Cationic Gum Derivative

The shampoo composition of the invention also comprises a cationic derivative of a polygalactomannan gum. The gum occurs naturally as guar gum, the principal component of the seed of the guar plant, *Cyamopsis tetragonalobus*. The guar molecule is essentially a straight chain mannan branched at quite regular intervals with single membered galactose units on alternate mannose units. The mannose units are linked to each other by means of beta (1-4) glycosidic linkages. The galactose branching is accomplished through an alpha (1-6) linkage. The cationic derivatives are obtained by reactions between the hydroxyl groups of the polygalactomannan and reactive quaternary ammonium compounds. The degree of substitution of the cationic groups is desirably at least 0.01 and preferably at least 0.05, for example from 0.08 to 0.5.

An example of a suitable quaternary ammonium derivative is hydroxypropyltrimethylammonium guar gum of the formula

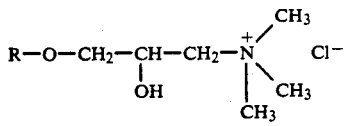

where R represents guar gum. Such a material is available commercially from Celanese-Stein Hall, USA under the name of Jaguar C13S; the word Jaguar is a trade mark. This material also has the CTFA designation guar hydroxypropyltrimonium chloride. In Jaguar C13S the degree of substitution of the cationic group is about 0.13. Another suitable material is that known as Jaguar C17 which is similar to Jaguar C13S but has a higher degree of substitution of cationic groups of about 0.25-0.31. A further example of a suitable guar derivative is the hydroxypropylated cationic guar derivative known as Jaguar C16 which as well as containing the above cationic quaternary ammonium groups also contains hydroxypropyl (—CH$_2$CH(OH)CH$_3$) substituent groups. In Jaguar C16 the degree of substitution of the cationic groups is 0.11-0.16 and the average number of moles of substitution of hydroxypropyl groups is 0.8-1.1.

The cationic polygalactomannan gum derivative is present in the shampoo of the invention in an amount of from 0.1 to 3% based on the weight of the shampoo. Preferred amounts are from 0.1% to 0.5% by weight.

If amounts of less than 0.1% by weight are used, little enhancement of sun protection is seen, and amounts of greater than 3% by weight are unlikely to further enhance the protection conferred by the sunscreen.

OTHER INGREDIENTS

The beneficial effects of the shampoo of the invention can be further enhanced by the addition of cosurfactants such as C$_{10}$-C$_{18}$ alkyl or alkylamido propyl betaine, C$_{10}$-C$_{18}$ fatty acid alkanolamide or mixtures thereof. Suitable co-surfactants are for example lauryl betaine, available as Empigen BB, cocamidopropyl betaine, available as Tegobetain L7, cocomonoethanolamide, available as Empilan CME, and cocodiethanolamide, available as Empilan CDE.

The co-surfactant may be added in an amount of from 0.5 to 7% by weight of the composition. An amount of less than 0.5% by weight gives little enhancement of the sun protection. It can be seen from Comparative Example 3 (below) and FIG. 3 that addition of up to 7% by weight of co-surfactant enhances the deposition of sunscreen on the hair. At levels of above 7% by weight, this effect is lost, and may even interfere with the deposition. The enhancement effect varies slightly with the specific co-surfactant used.

The shampoo composition of the invention may also include minor amounts of other ingredients which are commonly employed in shampoos. Examples of such ingredients are foam boosters, viscosity-adjusting agents, pacifiers, pearlescers, perfumes, dyes, colouring agents, conditioning agents, preservatives, thickeners, proteins, polymers and buffering agents.

USE OF THE SHAMPOO COMPOSITION

The shampoo composition of the invention is intended for use in the deposition of sunscreen materials on hair.

The composition is used in the same manner as conventional shampoo. The hair is wet, and a small quantity, for example from 1 to 5 ml is applied to the head. The wet hair is then rubbed with the hands to produce a lather which is then rinsed from the head. The procedure may be repeated.

BRIEF DESCRIPTION OF THE DRAWINGS

FIG. 3 shows the effect on deposition of Parsol MCX obtained by varying levels of co-surfactants. The co-surfactants tested were Tegobetain L7, Empigen BB and Empilan CDE.

COMPARATIVE EXAMPLES

Figure 1:
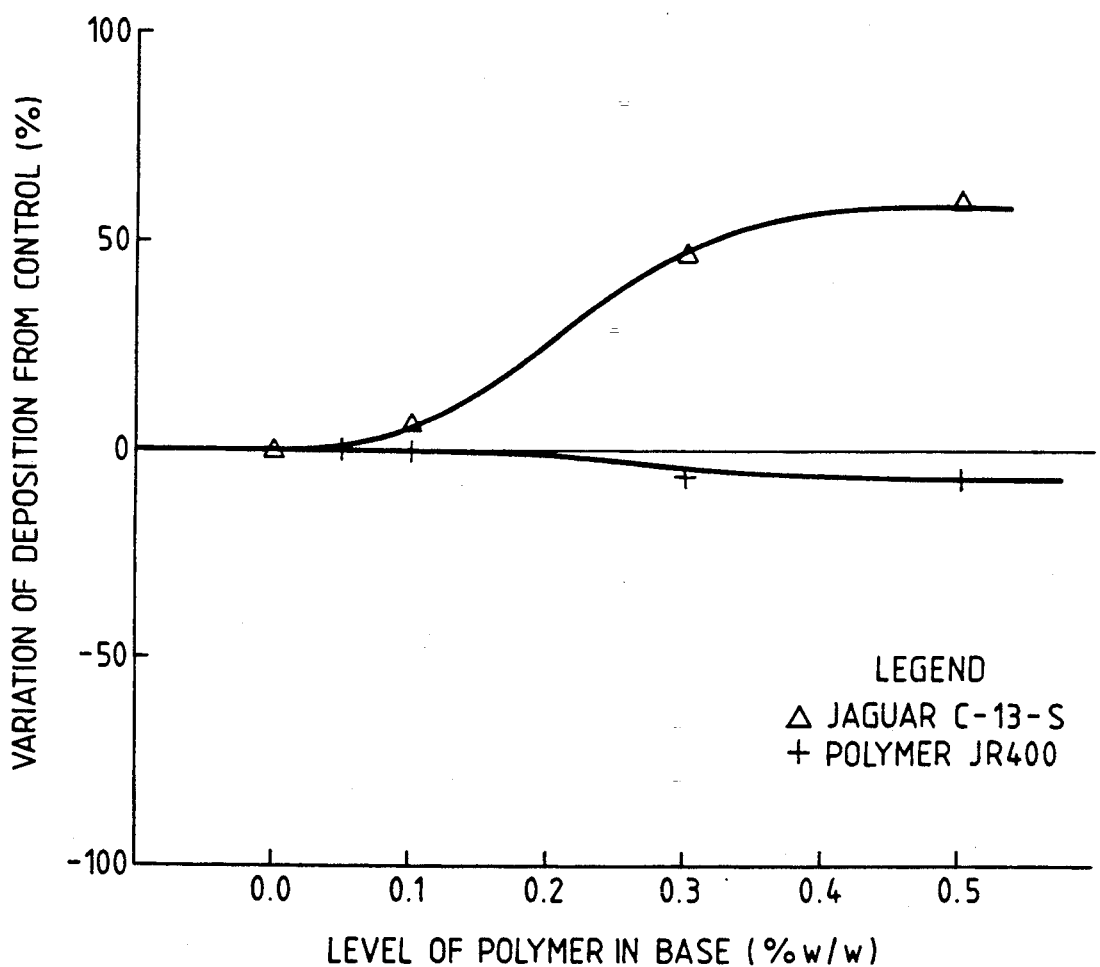
FIG. 1 shows the effect on deposition of parsol MCX sunscreen of increasing the level of cationic polymers, Jaguar C13S and Polymer JR 400.

The following procedure was followed in the Comparative Examples to determine the deposition of sunscreen on the hair.

Hair switches were cleaned thoroughly in surfactant, rinsed well and dried at 50° C. before using in the test procedure.

a) The switch was dampened with 3 g of water and inserted into a polythene bag (20 cm long, 4 cm wide, open at both ends). Test shampoo (0.25 g) was inserted into the bag, and the switch was massaged for 30 seconds, generating a foam which was retained within the bag. The switch was allowed to stand for 20 seconds, and was then rinsed by filling and emptying the bag 5 times with water (about 35° C.).

b) The excess moisture was removed by squeezing the switch within the bag between the fingers until about 3 g water remained. A further 0.25 g of test shampoo was inserted and the switch was again massaged for 30 seconds. After standing for 10 seconds, the switch was removed from the bag and was rinsed under running water (35° C.) for 30 seconds.

Excess moisture was removed by squeezing between the fingers, and the switch was dried in air at 50° C.

Switches were immersed in absolute ethanol (70 ml) for 120 minutes. After this time the alcohol was removed, the switches were rinsed with further ethanol (25 ml), and these two extracts were combined and made up to 100 ml in a volumetric flask. The spectrum of the sample was determined in the range 400-250 nm, and by comparison with standard spectra of sunscreens the amount deposited on the hair could be determined.

In the following Comparative Examples, all shampoo ingredients are given as weight percent.

COMPARATIVE EXAMPLE 1

The following shampoos were tested using the procedures set out above.

|  | Comparative Example 1 | | | | | | |
| --- | --- | --- | --- | --- | --- | --- | --- |
|  | Control | A | B | C | D | E | F |
| Ammonium lauryl sulphate | 16.0 | 16.0 | 16.0 | 16.0 | 16.0 | 16.0 | 16.0 |
| Jaguar C13S | — | 0.1 | 0.3 | 0.5 | — | — | — |
| Polymer JR 400+ | — | — | — | — | 0.1 | 0.3 | 0.5 |
| Parsol MCX | 2.0 | 2.0 | 2.0 | 2.0 | 2.0 | 2.0 | 2.0 |
| Water to | 100.0 | 100.0 | 100.0 | 100.0 | 100.0 | 100.0 | 100.0 |

+Polymer JR 400 - polymeric quaternary ammonium salt of hydroxyethyl cellulose.

The results are shown on FIG. 1 by plotting the percentage changes from the control value, and it can be seen that increasing the level of Polymer JR 400 in the shampoo slightly decreased the amount of Parsol MCX retained on the hair. However, the level of sunscreen retained is noticeably enhanced when increasing amounts of Jaguar C13S are included in the shampoo composition.

COMPARATIVE EXAMPLE 2

The following shampoos were tested using the procedure set out above.

|  | Control | H | J | K | L |
| --- | --- | --- | --- | --- | --- |
| SLES 2EO | 16.0 | 16.0 | 16.0 | 16.0 | 16.0 |
| Jaguar C13S | — | 0.3 | — | — | — |
| Jaguar C17 | — | — | 0.3 | — | — |
| Merquat 550+ | — | — | — | 0.3 | — |
| Jaguar HP60++ | — | — | — | — | 0.3 |
| Parsol MCX | 2.0 | 2.0 | 2.0 | 2.0 | 2.0 |
| Water to | 100.0 | 100.0 | 100.0 | 100.0 | 100.0 |

+Merquat 550 - polymeric quaternary ammonium salt consisting of acrylamide and dimethyl diallyl ammonium chloride monomers.
++Jaguar HP60 - (non-quaternary) propylene glycol ether of guar gum.

Figure 2:
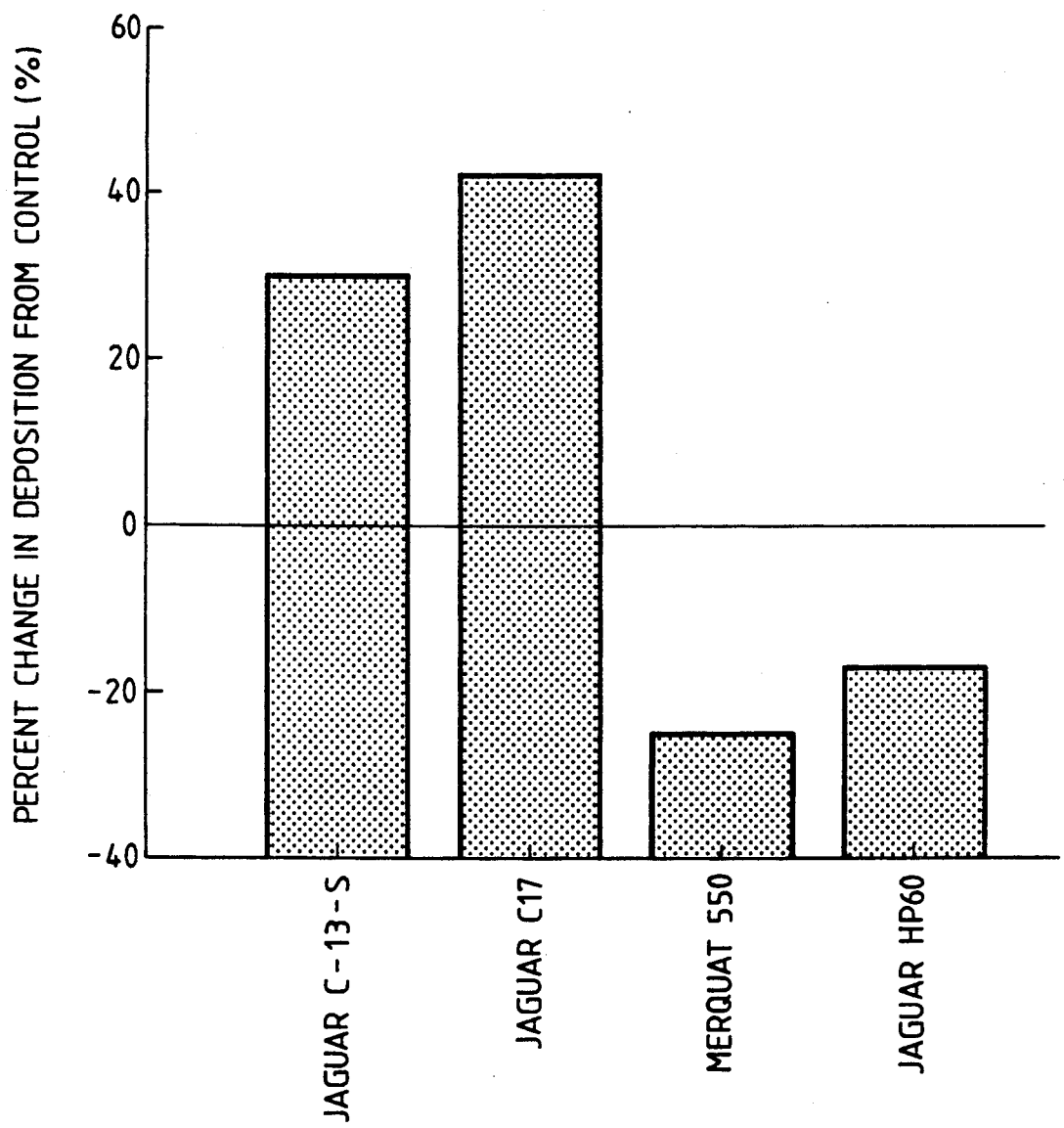
FIG. 2 shows the effect on retention of Parsol MCX on addition of the cationic polymers Jaguar C13S, Jaguar C17, Merquat 550 and the neutral galactomannan polymer Jaguar HP60 to a control composition.

The results were recorded on FIG. 2, as percentage change in deposition from the control composition, and it can be seen that derivatives of polygalactomannan gum, and particularly Jaguar C17, are very effective in enhancing the retention of sunscreen on the hair.

Merquat 550, which is a quaternary polymer but is not derived from polygalactomannan gum tends to suppress the retention of sunscreen, as does Jaguar HP60, which is a neutral derivative of polygalactomannan gum.

It can be concluded from FIGS. 1 and 2 that cationic polymers of polygalactomannan gum are unexpectedly effective in enhancing the retention of sunscreen on the hair from sunscreen containing shampoos.

COMPARATIVE EXAMPLE 3

The shampoos described in Table I were tested using the procedure set out above.

TABLE I

|  | 1a | | | | |
| --- | --- | --- | --- | --- | --- |
|  | Control | M | N | O | P |
| SLES 2EO | 14.0 | 10.0 | 7.0 | 4.0 | 0 |
| Jaguar C13S | 0.3 | 0.3 | 0.3 | 0.3 | 0.3 |
| Parsol MCX | 2.0 | 2.0 | 2.0 | 2.0 | 2.0 |
| Tegobetain L7+ | 0 | 4.0 | 7.0 | 10.0 | 14.0 |
| Water to | 100.0 | 100.0 | 100.0 | 100.0 | 100.0 |

|  | 1b | | | |
| --- | --- | --- | --- | --- |
|  | Q | R | S | T |
| SLES 2EO | 10.0 | 7.0 | 4.0 | 0 |
| Jaguar C13S | 0.3 | 0.3 | 0.3 | 0.3 |
| Parsol MCX | 2.0 | 2.0 | 2.0 | 2.0 |
| Empigen BB++ | 4.0 | 7.0 | 10.0 | 14.0 |

TABLE I-continued

| Water to | 100.0 | 100.0 | 100.0 | 100.0 |
| --- | --- | --- | --- | --- |

|  | 1c | | | |
| --- | --- | --- | --- | --- |
|  | U | V | W | X |
| SLES 2EO | 10.0 | 7.0 | 4.0 | 0 |
| Jaguar C13S | 0.3 | 0.3 | 0.3 | 0.3 |
| Parsol MCX | 2.0 | 2.0 | 2.0 | 2.0 |
| Empilan CDE+++ | 4.0 | 7.0 | 10.0 | 14.0 |
| Water to | 100.0 | 100.0 | 100.0 | 100.0 |

+Tegobetain L7 - cocamidopropyl betaine
++Empigen BB - lauryl betaine
+++Empilan CDE - cocodiethanolamide The results were plotted on FIG. 3 as percentage change in deposition of Parsol MCX from the control (containing no co-surfactant), for the shampoos containing varying amounts of Tegobetain L7, Empigen BB and Empilan CDE.

Total surfactant (surfactant plus co-surfactant) is kept at 14% wt. so that the effect of co-surfactant can be clearly seen.

FIG. 3 demonstrates the effect on sunscreen deposition of addition of co-surfactant to the shampoo composition. However, as has been stated earlier, addition of up to 7% by weight of co-surfactant enhances the deposition of sunscreen on the hair, while with amounts in excess of this level, this benefit is lost. This may be due to the co-surfactant interfering with deposition on the hair of the sunscreen. As can be seen from FIG. 3, the enhancement of deposition of sunscreen will vary slightly depending on the choice of co-surfactant.

The following Examples illustrate the invention.

EXAMPLES

|  | % wt |
| --- | --- |
| Example 1 | |
| Sodium lauryl ether sulphate (2EO) | 16.00 |
| Parsol MCX | 2.00 |
| Jaguar C13S | 0.20 |
| Formalin | 0.05 |
| Water to | 100.00 |
| Example 2 | |
| Sodium lauryl ether sulphate (3EO) | 10.00 |
| Tegobetain L7 | 4.00 |
| Jaguar C13S | 0.30 |
| Parsol MCX | 1.00 |
| Butylated Hydroxytoluene | 0.05 |
| Bronopol | 0.02 |
| Water to | 100.00 |
| Example 3 | |
| Sodium lauryl sulphate | 14.00 |
| Cocodiethanolamide | 3.00 |
| Jaguar C17 | 0.25 |
| Giv-Tan F | 1.50 |
| Formalin | 0.05 |
| Water to | 100.00 |
| Example 4 | |
| Ammonium lauryl sulphate | 12.00 |
| Empigen BB | 3.00 |
| Jaguar C17 | 0.50 |

|  | % wt |
|---|---|
| Neo-Heliopan E1000 | 2.00 |
| Butylated Hydroxytoluene | 0.05 |
| Bronopol | 0.02 |
| Water to | 100.00 |
| Example 5 | |
| Sodium lauryl ether sulphate (2EO) | 15.00 |
| Tegobetain L7 | 2.00 |
| Jaguar C13S | 0.35 |
| Parsol MCX | 2.00 |
| Eusolex 4360 | 1.00 |
| Formalin | 0.05 |
| Water to | 100.00 |
| Example 6 | |
| Sodium lauryl ether sulphate (3EO) | 10.00 |
| Empigen BB | 5.00 |
| Jaguar C16 | 0.20 |
| Neo-Heliopan E1000 | 1.50 |
| Parsol 1789 | 0.50 |
| Formalin | 0.05 |
| Water to | 100.00 |
| Example 7 | |
| Triethanolamine lauryl sulphate | 16.00 |
| Tegobetain L7 | 3.00 |
| Jaguar C13S | 0.50 |
| Giv-Tan F | 3.00 |
| Eusolex 8020 | 1.50 |
| Formalin | 0.05 |
| Water to | 100.00 |
| Example 8 | |
| Sodium lauryl sulphate | 16.00 |
| Empigen BB | 2.00 |
| Jaguar C17 | 0.20 |
| Neo-Heliopan E1000 | 1.50 |
| Uvinul D50 | 1.00 |
| Formalin | 0.05 |
| Water to | 100.00 |
| Example 9 | |
| Sodium lauryl ether sulphate (3EO) | 15.00 |
| Cocodiethanolamide | 2.50 |
| Empigen BB | 1.50 |
| Jaguar C13S | 0.20 |
| Parsol MCX | 1.50 |
| Eusolex 4360 | 1.00 |
| Butylated Hydroxytoluene | 0.05 |
| Bronopol | 0.02 |
| Water to | 100.00 |
| Example 10 | |
| Sodium lauryl ether sulphate (2EO) | 16.0 |
| Jaguar C13S | 0.3 |
| Empilan CME | 2.0 |
| Eusolex 4360 | 1.0 |
| Formalin | 0.05 |
| Water to | 100.0 |
| Example 11 | |
| Sodium lauryl ether sulphate (3EO) | 10.0 |
| Tegobetain L7 | 4.0 |
| Jaguar C13S | 0.25 |
| Isopropyl myristate | 1.0 |
| Parsol 1789 | 0.75 |
| Formalin | 0.05 |
| Water to | 100.0 |
| Example 12 | |
| Ammonium lauryl sulphate | 14.0 |
| Empigen BB | 3.0 |
| Jaguar C13S | 0.1 |
| Benzyl benzoate | 1.5 |
| Eusolex 4360 | 1.5 |
| Butylated hydroxytoluene | 0.05 |
| Bronopol | 0.02 |
| Water to | 100.0 |

I claim:

1. An aqueous shampoo composition comprising, in addition to water,
   a) from 2 to 40% by weight of an anionic surfactant;
   b) from 0.3 to 5% of a sunscreen that is water-insoluble and in liquid form at 20° C.; and
   c) from 0.1 to 3% of a cationic polygalactomannan gum which is a hydroxypropyltrimonium derivative thereof.

2. An aqueous shampoo composition according to claim 1 wherein the anionic surfactant is selected from the group consisting of $C_{10}$–$C_{18}$ alkyl sulphate, $C_{10}$–$C_{18}$ alkyl ether sulphate and mixtures thereof.

3. An aqueous shampoo composition according to claim 2 wherein the $C_{10}$–$C_{18}$ alkyl ether sulphate is selected from the group consisting of sodium lauryl ether sulphate (2EO) and sodium lauryl ether sulphate (3EO).

4. An aqueous shampoo composition according to claim 1 wherein the sunscreen material is present in an amount of from 0.3 to 2.0% by weight of the composition.

5. An aqueous shampoo composition according to claim 1 wherein the sunscreen is selected from the group consisting of 2-ethyl-hexyl-p-methoxycinnamate, 2-ethoxyethyl-p-methoxycinnamate and isoamyl-p-methoxycinnamate.

6. An aqueous shampoo composition according to claim 1, wherein the cationic derivative of a guar gum is present in an amount of from 0.1 to 0.5% by weight of the composition.

7. An aqueous shampoo composition according to claim 1, wherein the cationic derivative of a guar gum is guar hydroxypropyltrimonium chloride.

8. An aqueous shampoo composition according to claim 1, which further comprises a co-surfactant present in an amount of from 0.5 to 7% by weight of the composition.

9. An aqueous shampoo composition according to claim 8 wherein, the co-surfactant is selected from the group consisting of a $C_{10}$–$C_{18}$ alkyl betaine, a $C_{10}$–$C_{18}$ fatty acid alkanolamide, a $C_{10}$–$C_{18}$ alkylamidopropyl betaine and mixtures thereof.

10. An aqueous shampoo composition according to claim 8, wherein the co-surfactant is selected from the group of cocamidopropyl betaine, cocomonoethanolamide, cocodiethanolamide, lauryl dimethyl betaine and mixture thereof.

11. An aqueous shampoo composition comprising, in addition to water,
    a) from 2 to 40% by weight of an anionic surfactant selected from the group consisting of $C_{10}$–$C_{18}$ alkyl sulphate, $C_{10}$–$C_{18}$ alkyl ether sulphate and mixtures thereof;
    b) from 0.3 to 5% of a sunscreen selected from the group consisting of water-insoluble sunscreens selected from the group consisting of 2-ethyl-hexyl-pmethoxycinnamate, 2-ethoxyethyl p-methoxycinnamate and isoamyl-p-methoxycinnamate;
    c) from 0.1 to 3% of a cationic polygalactomannan gum which is a hydroxypropyltrimonium derivative thereof; and
    d) from 0.5 to 7% of a co-surfactant selected from the group consisting of $C_{10}$–$C_{18}$ alkyl betaine, $C_{10}$–$C_{18}$ fatty acid alkanolamide, $C_{10}$–$C_{18}$ alkylamidopropyl betaine and mixture thereof.

* * * * *